US010345474B2

United States Patent
Lin et al.

(10) Patent No.: US 10,345,474 B2
(45) Date of Patent: Jul. 9, 2019

(54) ANTI-SATURATION DEVICE AND METHOD FOR GROUND MAGNETIC RESONANCE SIGNAL AMPLIFYING CIRCUIT

(71) Applicant: JILIN UNIVERSITY, Changchun, Jilin (CN)

(72) Inventors: Tingting Lin, Changchun (CN); Yang Zhang, Changchun (CN); Xu Shu, Changchun (CN); Jun Lin, Changchun (CN); Ling Wan, Changchun (CN); Jing Zhao, Changchun (CN); Xin Cai, Changchun (CN)

(73) Assignee: Jilin University, Changchun, Jilin (CN)

( * ) Notice: Subject to any disclaimer, the term of this patent is extended or adjusted under 35 U.S.C. 154(b) by 140 days.

(21) Appl. No.: 15/442,430

(22) Filed: Feb. 24, 2017

(65) Prior Publication Data

US 2017/0336524 A1 Nov. 23, 2017

(30) Foreign Application Priority Data

May 20, 2016 (CN) .......................... 2016 1 0340100

(51) Int. Cl.
*G01V 3/14* (2006.01)
*G01R 33/36* (2006.01)

(52) U.S. Cl.
CPC ........... *G01V 3/14* (2013.01); *G01R 33/3614* (2013.01); *Y02A 90/344* (2018.01)

(58) Field of Classification Search
USPC .................. 324/300–322, 629; 600/128–131
See application file for complete search history.

(56) References Cited

U.S. PATENT DOCUMENTS

| 6,956,371 B2 * | 10/2005 | Prammer | G01N 24/081 324/300 |
| 2004/0008027 A1 * | 1/2004 | Prammer | G01N 24/081 324/303 |

(Continued)

FOREIGN PATENT DOCUMENTS

| CN | 101771386 B | 9/2012 |
| CN | 203251284 U | 10/2013 |

(Continued)

OTHER PUBLICATIONS

Analysis and Research on FID Signal Amplification Circuit of Low Field Magnetic Resonance.

(Continued)

*Primary Examiner* — Melissa J Koval
*Assistant Examiner* — Tiffany A Fetzner
(74) *Attorney, Agent, or Firm* — Knobbe, Martens, Olson & Bear, LLP

(57) ABSTRACT

An anti-saturation device for a ground magnetic resonance signal amplifying circuit has a receiving coil connected with a band-pass filter circuit through a pre-amplifying circuit and a programmable amplifying circuit. The programmable amplifying circuit is connected with an AD acquisition card through the band-pass filter circuit. The band-pass filtering circuit is connected with a computer through the AD acquisition card, and the AD acquisition card is connected with an emitting system through the computer. An automatic amplification factor adjusting module is embedded into a nuclear magnetic resonance detector, and can also directly replace a receiving amplification circuit of the nuclear magnetic resonance detector to work independently.

2 Claims, 2 Drawing Sheets

(56) References Cited

U.S. PATENT DOCUMENTS

2016/0124041 A1* 5/2016 Pathak ................... G01R 29/08
                                                                324/629
2016/0294313 A1   10/2016 Chassard et al.
2017/0336524 A1* 11/2017 Lin ..................... G01R 33/3614

FOREIGN PATENT DOCUMENTS

| CN | 104485906 A  | 4/2015  |
| CN | 103323860 B  | 9/2015  |
| CN | 204719240 U  | 10/2015 |
| FR |   3013528 A1 | 5/2015  |
| KR | 100787081 B1 | 12/2007 |

OTHER PUBLICATIONS

First Office Action dated Oct. 31, 2016, received in corresponding Chinese Application No. 201610340100.8.

* cited by examiner

ANTI-SATURATION DEVICE AND METHOD FOR GROUND MAGNETIC RESONANCE SIGNAL AMPLIFYING CIRCUIT

INCORPORATION BY REFERENCE TO ANY PRIORITY APPLICATIONS

This application is the U.S. non-provisional application claiming priority to Chinese Patent Application No. 201610340100.8, filed May 20, 2016. Any and all applications for which a foreign or domestic priority claim is identified in the Application Data Sheet as filed with the present application are hereby incorporated by reference under 37 CFR 1.57.

TECHNICAL FIELD

The present disclosure relates to a nuclear magnetic resonance groundwater detector, and in particular to an anti-saturation device and an anti-saturation method for a magnetic resonance signal amplification circuit.

BACKGROUND

The nuclear magnetic resonance (MRS) groundwater detection technology is developed for detecting groundwater directly and non-destructively in the field of geophysics at present. After the groundwater is excited by an alternating magnetic field, a nuclear magnetic resonance signal is generated. The signal is an exponentially decaying sine wave signal, which is also referred to as a free induction decay (FID) signal. The FID signal is usually in a nano-volt (nV) level, which may be detected after thousands or tens of thousands of times amplification. The signal is also apt to be interfered by an electromagnetic noise from the external environment. The interference noises of different test areas are different, and even in the same test area, the electromagnetic interference noises are also different at different times. In an amplification device for a conventional nuclear magnetic resonance detection system, an amplification factor is set only once based on experience before working. However, it will take two hours to complete a test at a test point. The environmental noise changes greatly, especially in an area having strong noise interference. Therefore, the amplifying circuit is apt to be saturated, thus failing to acquire valid data. For this reason, it is difficult to achieve a desired result by using the same amplification factor when testing in different regions or in the same region but at different times. The amplifier having a fixed amplification factor is apt to be saturated, resulting in signal distortion especially in the case of complex environments with serious noise interference. Therefore, in order to prevent the saturation of the amplifier while meeting the FID signal amplification requirements, it is of great significance to design an anti-saturation device for a ground magnetic resonance signal amplifying circuit.

SUMMARY

One object of the present disclosure is to provide an anti-saturation device for a ground magnetic resonance signal amplifying circuit to overcome the above drawback in the conventional technology.

The other object of the present disclosure is to provide an anti-saturation method for the anti-saturation device for the ground magnetic resonance signal amplifying circuit.

The above object is achieved through the following technical solution:

An anti-saturation device for a ground magnetic resonance signal amplifying circuit includes: a receiving coil 1, a pre-amplifying circuit 2, a programmable amplifying circuit 3, a band-pass filter circuit 4, an analog-digital (AD) acquisition card 5, a computer 6, a micro control unit (MCU) control circuit 7, a level transition and electrical isolating circuit 8 and an emitting system 9, where the receiving coil 1 is connected with the band-pass filter circuit 4 through the pre-amplifying circuit 2 and the programmable amplifying circuit 3; the programmable amplifying circuit 3 is connected with the AD acquisition card 5 through the band-pass filter circuit 4; the band-pass filter circuit 4 is connected with the computer 6 through the AD acquisition card 5; the AD acquisition card 5 is connected with the emitting system 9 through the computer 6; the computer 6 is connected with the level transition and electrical isolating circuit 8 through the MCU control circuit 7; and the level transition and electrical isolating circuit 8 is connected with the programmable amplifying circuit 3.

The AD acquisition card 5 includes an analog-digital converter (ADC) module 10, a level transition and electrical isolating circuit 11, a field programmable gate array (FPGA) module 12, a random access memory (RAM) module 13, a read only memory (ROM) module 14, a network interface 15 and a serial communication interface (SCI) 16, where the ADC module 10 is connected with the FPGA module 12 through the level transition and electrical isolating circuit 11; the RAM module 13 is connected with the ROM module 14 through the FPGA module 12; the FPGA module 12 is connected with the network interface 15 and the SCI 16.

The computer is connected with the network interface 15 and the SCI 16.

An anti-saturation method for the anti-saturation device for a ground magnetic resonance signal amplifying circuit, includes:

step a: setting a programmable amplification factor, and an preset upper limit value $V_H$ and a preset lower limit value $V_L$ for overall signals manually based on an ambient noise intensity at a to-be-detected location before a nuclear magnetic resonance water detection system starts working;

step b: performing acquisition in an acquisition time of 256 ms with 6400 sampling points, and calculating, by the computer 6, a maximum absolute value $V_{max}$ among absolute values of 6400 acquisition points based on all signals collected by the AD acquisition card 5;

step c: transmitting the $V_{max}$ to the MCU control circuit 7 by the computer 6, where the amplification factor for the present time is denoted as $A_i$; comparing, by the MCU control circuit 7, the $V_{max}$ with the preset upper limit value and the preset lower limit value; and calculating the amplification factor for the next adjustment as: $A_{i+1}=3.2*A_i/V_{max}$, to reduce the amplification factor, in a case that the $V_{max}$ is greater than the preset upper limit value $V_H$, and increase the amplification factor in a case that the $V_{max}$ is less than the preset lower limit value $V_L$. Since the amplification factor of the programmable amplifier may be selected from an arithmetic sequence from 2000 to 32000 with an equal difference of 2000, totaling 16 discrete integer point amplification factors, an adjusted magnification factor for next adjustment is selected to be the integer amplification factor which is nearest to and not greater than the amplification factor $A_{i+1}$. For example, if $A_{i+1}=5130$, the actual amplification factor for the next time is selected as 4000 times.

step d: setting the amplification factor of the programmable amplifying circuit 3 as the adjusted magnification factor, by the MCU control circuit 7 through the level transition and electrical isolating circuit 8, where the set amplification factor serves as the amplification factor for acquired signals for the next time;

step e: transmitting, by the MCU control circuit 7, a complete instruction to the computer 6 after setting the amplification factor setting; and controlling, by the computer 6, the emitting system 9 to perform a next excitation; and step f: repeating the step b to e until stopping acquisition.

Advantageous effects of the present disclosure are as follows. An automatic amplification factor adjusting module is embedded into a nuclear magnetic resonance detector, and may also directly replace a receiving amplification circuit of the nuclear magnetic resonance detector to work independently. Optimal amplification factors are set through the anti-saturation device in a complex environment with severe noise interference, so that the issues that signals are distorted or the amplification factor is not sufficient as only one amplification factor is used can be solved. Since the whole amplification factor adjusting process is automatically performed, the ground water exploration efficiency is improved. The anti-saturation method is simple to implement, has a small calculation amount, and requires a low amplification factor adjusting speed.

Figure 1:
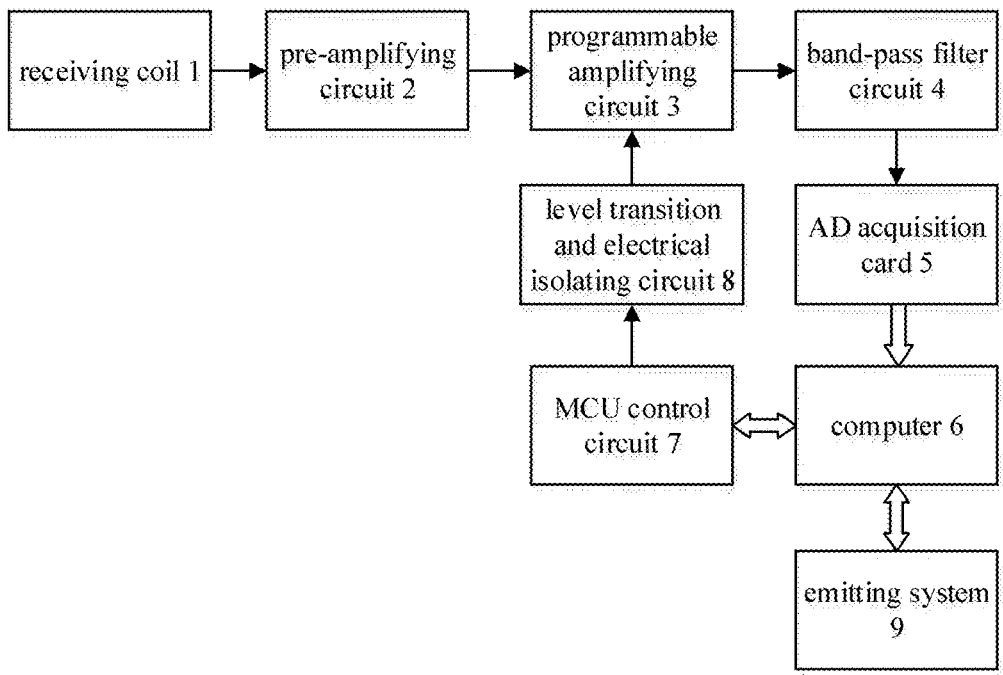
FIG. 1 is a structure diagram of an anti-saturation device for a ground magnetic resonance signal amplifying circuit.

Reference numbers in the Figures are described as follows: 1, receiving coil; 2, pre-amplifying circuit; 3, programmable amplifying circuit; 4, band-pass filter circuit; 5, AD acquisition card; 6, computer; 7, MCU control circuit; 8, level transition and electrical isolating circuit; 9, emitting system; 10, ADC module; 11, level transition and electrical isolating circuit; 12, FPGA module; 13, RAM module; 14, ROM module; 15, network interface; and 16, SCI interface.

DETAILED DESCRIPTION OF THE INVENTION

Hereinafter, the present disclosure will be described in detail in conjunction with drawings and embodiments.

An anti-saturation device for a ground magnetic resonance signal amplifying circuit includes: a receiving coil 1, a pre-amplifying circuit 2, a programmable amplifying circuit 3, a band-pass filter circuit 4, an analog-digital (AD) acquisition card 5, a computer 6, a micro control unit (MCU) control circuit 7, a level transition and electrical isolating circuit 8 and an emitting system 9. The receiving coil 1 is connected with the band-pass filter circuit 4 through the pre-amplifying circuit 2 and the programmable amplifying circuit 3. The programmable amplifying circuit 3 is connected with the AD acquisition card 5 through the band-pass filter circuit 4. The band-pass filter circuit 4 is connected with the computer 6 through the AD acquisition card 5. The AD acquisition card 5 is connected with the emitting system 9 through the computer 6. The computer 6 is connected with the level transition and electrical isolating circuit 8 through the MCU control circuit 7. The level transition and electrical isolating circuit 8 is connected with the programmable amplifying circuit 3.

The AD acquisition card 5 includes an analog-digital converter (ADC) module 10, a level transition and electrical isolating circuit 11, a field programmable gate array (FPGA) module 12, a random access memory (RAM) module 13, a read only memory (ROM) module 14, a network interface 15 and a serial communication interface (SCI) 16. The ADC module 10 is connected with the FPGA module 12 through the level transition and electrical isolating circuit 11. The RAM module 13 is connected with the ROM module 14 through the FPGA module 12. The FPGA module 12 is connected with the network interface 15 and the SCI interface 16.

The computer 6 is connected with the network interface 15 and the SCI interface 16.

An anti-saturation method applied in the anti-saturation device for a ground magnetic resonance signal amplifying circuit includes steps a to f.

In step a, a programmable amplification factor, and an preset upper limit value $V_H$ and a preset lower limit value $V_L$ for overall signals are set manually based on an ambient noise intensity at a to-be-detected location before a nuclear magnetic resonance water detection system starts working.

In step b, acquisition is performed in an acquisition time of 256 ms with 6400 sampling points, and a maximum absolute value $V_{max}$ among absolute values of 6400 acquisition points is calculated by the computer 6 based on all signals collected by the AD acquisition card 5.

In step c, the $V_{max}$ is transmitted to an MCU control circuit 7 by the computer 6, the amplification factor for the present time is denoted as $A_i$, the $V_{max}$ is compared with the preset values in the MCU, and the amplification factor for the next adjustment is calculated as: $A_{i+1}=3.2*A_i/V_{max}$, to reduce the amplification factor in a case that the $V_{max}$ is greater than the preset upper limit value $V_H$, and increase the amplification factor in a case that the $V_{max}$ is less than the preset lower limit value $V_L$. Since the amplification factor of the programmable amplifier may be selected from an arithmetic sequence: 2000, 4000, 6000 . . . 30000, 32000 with an equal difference of 2000, totaling 16 discrete integer amplification factors, an adjusted magnification factor is selected to be the integer amplification factor which is nearest to and not greater than the amplification factor $A_{i+1}$. For example, if $A_{i+1}=5130$, the actual amplification factor for the next time is selected as 4000 times.

In step d, the amplification factor of the programmable amplifying circuit 3 is set as the adjusted magnification factor, by the MCU control circuit 7 through the level transition and electrical isolating circuit 8. The set amplification factor serves as the amplification factor for acquired signals for the next time.

In step e, a complete instruction is transmitted by the MCU control circuit 7 to the computer 6 after the amplification factor is set, and the emitting system 9 is controlled by the computer 6 to perform a next excitation.

In step f, the step b to e are repeated until stopping acquisition.

As shown in FIG. 1, the anti-saturation device for a ground magnetic resonance signal amplifying circuit includes a receiving coil 1, a pre-amplifying circuit 2, a programmable amplifying circuit 3, a band-pass filter circuit 4, an AD acquisition card 5, a computer 6, an MCU control circuit 7, a level transition and electrical isolating circuit 8 and an emitting system 9. The receiving coil 1 is connected with the band-pass filter circuit 4 through the pre-amplifying circuit 2 and the programmable amplifying circuit 3. The programmable amplifying circuit 3 is connected with the AD acquisition card 5 through the band-pass filter circuit 4. The band-pass filter circuit 4 is connected with the computer 6 through the AD acquisition card 5. The AD acquisition card 5 is connected with the emitting system 9 through the computer 6. The computer 6 is connected with the level transition and electrical isolating circuit 8 through the MCU control circuit 7. The level transition and electrical isolating circuit 8 is connected with the programmable amplifying circuit 3.

Figure 2:
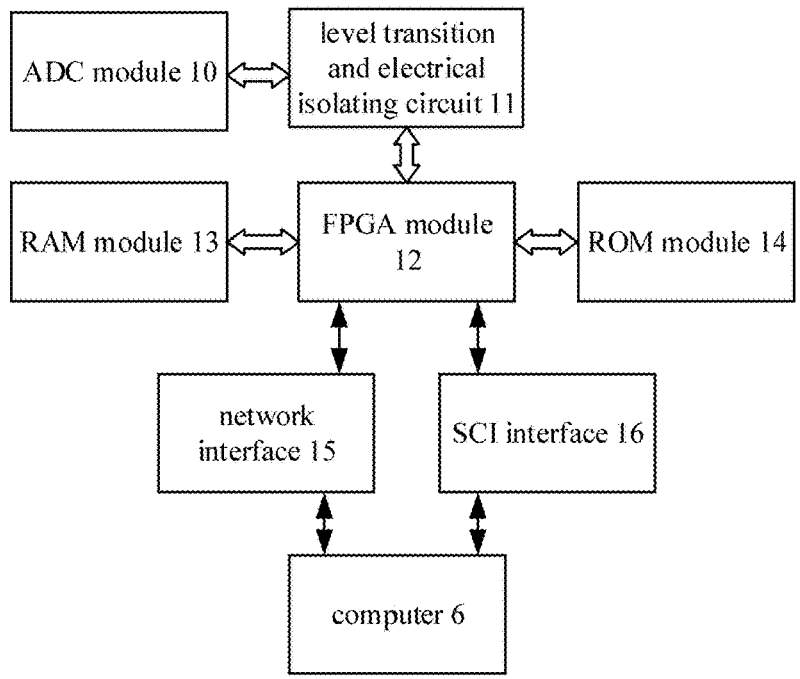
FIG. 2 is a structure diagram of an AD acquisition card 5 in FIG. 1.

As shown in FIG. 2, the AD acquisition card 5 includes an ADC module 10, a level transition and electrical isolating circuit 11, an FPGA module 12, an RAM module 13, an ROM module 14, a network interface 15 and an SCI interface 16. The FPGA module 12 is connected with the ADC module 10 through the level transition and electrical isolating circuit 11. The RAM module 13 is connected with the ROM module 14 through the FPGA module 12. The FPGA module 12 is connected with the network interface 15 and the SCI interface 16.

The computer 6 is connected with the network interface 15 and the SCI interface 16.

The ground magnetic resonance signals are induced by the receiving coil 1, and are inputted to the AD acquisition card 5 through the pre-amplifying circuit 2, the programmable control amplifying circuit 3 and the band-pass filter circuit 4. The ADC module 10 is controlled by the FPGA module 12 to transmit the acquired ground magnetic resonance signals to the computer 6. The computer 6 processes the signals to obtain the maximum evaluation value. The evaluation value is transmitted to the MCU control circuit 7 to compare the evaluation value with the preset values. The amplification factor is reduced in a case that the evaluation value is greater than the preset upper limit value, and is increased in a case that the evaluation value is less than the preset lower limit value. The above process is repeated by setting the amplification factor of a next excitation based on the data collected for the present time, until the end of work.

An anti-saturation method applied in the anti-saturation device for a ground magnetic resonance signal amplifying circuit includes steps a to f.

In step a, a programmable amplification factor, and an preset upper limit value $V_H$ and a preset lower limit value $V_L$ for overall signals are set manually based on an ambient noise intensity at a to-be-detected location before a nuclear magnetic resonance water detection system starts working.

In step b, acquisition is performed in an acquisition time of 256 ms with 6400 sampling points, and a maximum absolute value $V_{max}$ among absolute values of 6400 acquisition points is calculated by the a computer 6 based on all signals collected by the AD acquisition card 5.

In step c, the $V_{max}$ is transmitted to an MCU control circuit 7 by the computer 6, the amplification factor for the present time is denoted as $A_i$, the $V_{max}$ is compared with the preset values in an MCU, and the amplification factor for the next adjustment is calculated as: $A_{i+1}=3.2*A_i/V_{max}$, to reduce the amplification factor in a case that the $V_{max}$ is greater than the preset upper limit value $V_H$, and increase the amplification factor in a case that the $V_{max}$ is less than the preset lower limit value $V_L$. Since the amplification factor of the programmable amplifier may be selected from an arithmetic sequence: 2000, 4000, 6000 . . . 30000, 32000 with an equal difference of 2000, totaling 16 discrete integer point amplification factors, an adjusted magnification factor is selected to be the integer amplification factor which is nearest to and not greater than the amplification factor $A_{i+1}$. For example, if $A_{i+1}=5130$, the actual amplification factor for the next time is selected as 4000 times.

In step d, the amplification factor of the programmable amplifying circuit 3 is set as the adjusted magnification factor, by the MCU control circuit 7 through a level transition and electrical isolating circuit 8. The set amplification factor serves as the amplification factor for acquired signals for the next time.

In step e, a complete instruction is transmitted by the MCU control circuit 7 to the computer 6 after setting the amplification factor, and the emitting system 9 is controlled by the computer 6 to perform a next excitation.

In step f, the step b to e are repeated until stopping acquisition.

Embodiment

The application of the anti-saturation device for the ground magnetic resonance signal amplifying circuit is described with an example of detecting, in the North Lake Wetland Park in Changchun, with a nuclear magnetic resonance groundwater detection system having a transmitting coil and a receiving coil both of a size of 50 m*50 m, and arranged with the anti-saturation device.

In step a, an initial amplification factor of 20000 times, an preset upper limit value $V_H=4V$ and a preset lower limit value $V_L=0.5V$ are set manually through the computer 6 based on an ambient noise intensity at a to-be-detected location before the nuclear magnetic resonance water detection system starts working.

In step b, acquisition is performed in an acquisition time of 256 ms with 6400 sampling points, and a maximum absolute value $V_{max}$ among absolute values of 6400 acquisition points is calculated by the computer 6 based on all signals collected by the AD acquisition card 5.

In step c, the $V_{max}$ is transmitted to an MCU control circuit 7 by the computer 6, the amplification factor for the present time is denoted as $A_i$, the $V_{max}$ is compared with the preset values in an MCU, and the amplification factor for the next adjustment is calculated as: $A_{i+1}=3.2*A_i/V_{max}$, to reduce the amplification factor in a case that the $V_{max}$ is greater than the preset upper limit value $V_H$, and increase the amplification factor in a case that the $V_{max}$ is less than the preset lower limit value $V_L$. Since the amplification factor of the programmable amplifier may be selected from an arithmetic sequence: 2000, 4000, 6000 . . . 30000, 32000 with an equal difference of 2000, totaling 16 discrete integer point amplification factors, an adjusted magnification factor is selected to be the integer amplification factor which is nearest to and not greater than the amplification factor $A_{i+1}$. For example, if $A_{i+1}=5130$, the actual amplification factor for the next time is selected as 4000 times.

Figure 3:
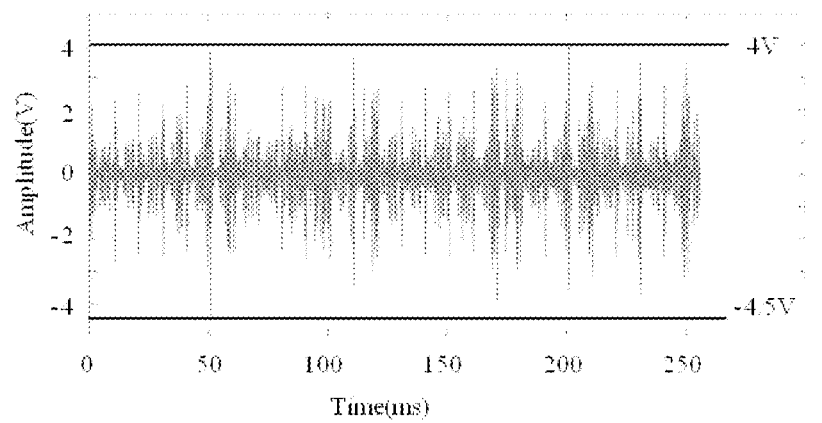
FIG. 3 is a time-domain diagram of signals acquired in a first acquisition according to an embodiment.

The result of the first data acquisition is shown in FIG. 3. $V_{max}=4.5V$ is calculated by the anti-saturation device automatically. Since $V_{max}>V_H$, i.e., $V_{max}$ is greater than the upper limit of the preset value, the amplification factor need to be reduced. As $A_{i+1}=3.2*A_i/V_{max}=14222$, the actual amplification factor of the programmable amplifier is set as 14,000 times.

In step d, the amplification factor of the programmable amplifying circuit 3 is set as the adjusted magnification factor, by the MCU control circuit 7 through the level transition and electrical isolating circuit 8. The set amplification factor serves as the amplification factor for acquired signals for the next time.

In step e: the MCU control circuit 7 transmits a complete instruction to the computer 6 after setting the amplification factor, and the computer 6 controls the emitting system 9 to perform a next excitation.

Figure 4:
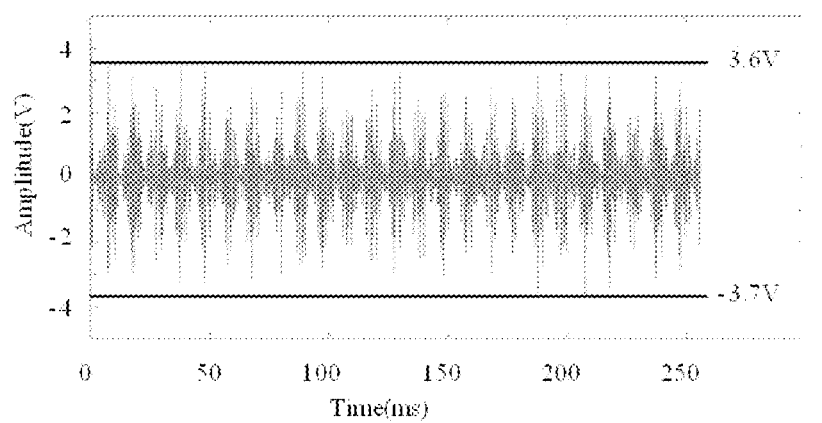
FIG. 4 is a time-domain diagram of signals acquired in a second acquisition according to an embodiment.

The result of the second data acquisition is shown in FIG. 4, in which the maximum absolute value $V_{max}=3.7V$, and $V_L<V_{max}<V_H$, which means the signals is between the upper preset value and lower preset value, not only meeting the requirement for amplifying signals but also avoiding the amplifier saturation problem in the case of single amplification factor.

In step f: the step b to e are repeated until stopping acquisition.

What is claimed is:

1. An anti-saturation device for utilized with a ground nuclear magnetic resonance (NMR) signal amplifying circuit, the ground nuclear magnetic resonance signal amplifying circuit comprising:
   a ground nuclear magnetic resonance receiving coil;
   a pre-amplifying circuit;
   a programmable amplifying circuit;
   a band-pass filter circuit; and
   an emitting system;
wherein the anti-saturation device comprises:
   an analog-digital (AD) acquisition card;
   a computer;
   a micro control unit (MCU) control circuit; and
   a level transition and electrical isolating circuit;
   wherein the anti-saturation device utilized with the ground nuclear magnetic resonance signal amplifying circuit has the ground nuclear magnetic resonance receiving coil connected with the emitting system through the pre-amplifying circuit, the programmable amplifying circuit, the band-pass filter circuit, the AD acquisition card and the computer in the sequence listed;
   the programmable control amplifying circuit is connected with the MCU control circuit through the electrical isolating circuit;
   the MCU control circuit is connected with the computer;
   the AD acquisition card comprises:
      an analog-digital converter (ADC) module,
      a level transition and electrical isolating circuit,
      a field programmable gate array (FPGA) module,
      a random access memory (RAM) module,
      a read only memory (ROM) module,
      a network interface and
      a serial communication interface (SCI);
   wherein the ADC module is connected with the FPGA module through the level transition and the electrical isolating circuit;
      the RAM module is connected with the ROM module through the FPGA module;
      the FPGA module is connected with the network interface and the SCI; and
      the network interface and the SCI are connected with the computer,
   whereby this configuration of components connected into the ground nuclear magnetic resonance amplification circuit forms the anti-saturation device because:
   the ground nuclear magnetic resonance receiving coil is configured to induce ground magnetic resonance signals and transmit the ground magnetic resonance signals to the AD acquisition card through the pre-amplifying circuit, the programmable control amplifying circuit and the band-pass filter circuit;
   the AD acquisition card is configured to perform a ground NMR acquisition in an acquisition time of 256 ms with 6400 sampling points;
   the computer is configured to calculate a maximum absolute value $V_{max}$ among absolute values of 6400 acquisition points based on all signals collected by the AD acquisition card, and transmit the $V_{max}$ to the MCU control circuit;
   the MCU control circuit is configured to:
      a) compare the $V_{max}$ with the preset upper limit value and the preset lower limit value;
      b) calculate the amplification factor for the next adjustment as: $A_{i+1}=3.2*A_i/V_{max}$, in order to reduce the amplification factor in a case that the $V_{max}$ is greater than the preset upper limit value $V_H$, and increase the amplification factor in a case that the $V_{max}$ is less than the preset lower limit value $V_L$, wherein the amplification factor for the present time is denoted as $A_i$;
      c) select an adjusted magnification factor as the integer amplification factor which is nearest to and not greater than the amplification factor $A_{i+1}$ from an arithmetic sequence from 2000 to 32000 with an equal difference of 2000, totaling 16 discrete integer point amplification factors;
      d) set, through the level transition and electrical isolating circuit of the anti-saturation device, the amplification factor of the programmable amplifying circuit as the adjusted magnification factor, wherein the set amplification factor serves as the amplification factor for acquired signals for the next adjustment to the ground NMR acquisition occurring in time; and
      e) transmit a complete instruction to the computer after setting the amplification factor; and
   wherein the computer is further configured to control the emitting system to perform a next excitation.

2. An anti-saturation method compatible with an anti-saturation device that is utilized with a ground water nuclear magnetic resonance (NMR) signal amplifying circuit, comprising the steps of:
   a) setting a programmable amplification factor, and an preset upper limit value $V_H$ and a preset lower limit value $V_L$ for overall signals manually based on an ambient noise intensity at a to-be-detected location before a nuclear magnetic resonance (NMR) ground water detection system starts working;
   b) performing a ground water NMR acquisition in an acquisition time of 256 ms with 6400 sampling points, and calculating, by a computer, a maximum absolute value $V_{max}$ among absolute values of 6400 acquisition points based on all signals collected by an AD acquisition card;
   c) obtaining an adjusted amplification factor, comprising:
      transmitting the $V_{max}$ to a micro control unit (MCU) control circuit by the computer, wherein the amplification factor for the present time is denoted as $A_i$;
      comparing, by the MCU control circuit, the $V_{max}$ with the preset upper limit value and the preset lower limit value; and
      calculating the amplification factor for the next adjustment as: $A_{i+1}=3.2*A_i/V_{max}$, in order to reduce the amplification factor in a case that the $V_{max}$ is greater than the preset upper limit value $V_H$, and increase the amplification factor in a case that the $V_{max}$ is less than the preset lower limit value $V_L$; and
      selecting an adjusted magnification factor as the integer amplification factor which is nearest to and not greater than the amplification factor $A_{i+1}$ from an arithmetic sequence from 2000 to 32000 with an equal difference of 2000, totaling 16 discrete integer point amplification factors;

d) setting the amplification factor of a programmable amplifying circuit as the adjusted magnification factor, by the MCU control circuit through a level transition and electrical isolating circuit, wherein the set amplification factor serves as the amplification factor for acquired signals for the next adjustment to the ground NMR acquisition occurring in time;

e) transmitting, by the MCU control circuit, a complete instruction to the computer after setting the amplification factor; and controlling, by the computer, the emitting system to perform a next excitation; and f) repeating said step b) performing to step e) transmitting until stopping acquisition of the nuclear magnetic resonance signals.

\* \* \* \* \*